United States Patent [19]

Prodo et al.

[11] 4,077,990

[45] Mar. 7, 1978

[54] SURFACE-ACTIVE AGENT

[75] Inventors: Kenneth W. Prodo, Westfield; Robert W. Bender, Jersey City, both of N.J.

[73] Assignee: Kewanee Industries, Bryn Mawr, Pa.

[21] Appl. No.: 735,693

[22] Filed: Oct. 26, 1976

[51] Int. Cl.$^2$ .............................................. C09S 5/00
[52] U.S. Cl. ................................................ 260/404.5
[58] Field of Search ............... 260/404.5 R, 404.5 PA, 260/404.5 N

[56] References Cited

U.S. PATENT DOCUMENTS

| | | | |
|---|---|---|---|
| 2,609,381 | 9/1952 | Goldstein et al. | 260/404.5 PA |
| 2,805,135 | 9/1957 | Bell et al. | 260/404.5 PA |
| 3,206,512 | 9/1965 | Koebner et al. | 260/404.5 R |
| 3,356,727 | 12/1967 | Koebner et al. | 260/404.5 R |

*Primary Examiner*—Winston A. Douglas
*Assistant Examiner*—John F. Niebling
*Attorney, Agent, or Firm*—Arthur A. Jacobs

[57] ABSTRACT

10-undecylenoylamidopropyl dimethylamine oxide utilizable as a surfactant and as an intermediate for synthesizing other surfactants.

1 Claim, No Drawings

SURFACE-ACTIVE AGENT

The present invention relates to a surfactant, and it particularly relates to the compound 10-undecylenoylamidopropyl dimethylamine oxide of the formula:

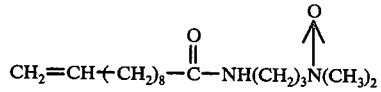

The above compound differs from previously prepared amidopropylamine oxides in that it has an unsaturated vinyl moiety at the very end of the alkenoylamido chain. This confers chemical and physical properties of the new compound which are different from any previously prepared amidopropylamine oxides in that this amine oxide is "softer" and has better "slip" properties than other previously prepared amidopropylamine oxides, thereby making it a better surfactant for many products, and especially for certain cosmetic products, particularly creams and lotions.

Since the vinyl unsaturation of the present compound is a terminal moiety, it can be subjected to a large number of one, two or three-step syntheses which extend the length of the amido group without producing undesirable lengthy side chains, such as would occur if the unsaturation were in the middle of the amido chain. Additions to chains with internally located unsaturation result in branching, so that a good part of the organic portion becomes a branch and does not contribute to the new chain length.

The syntheses that extend the chain length of the 10-undecylenoylamido group usually introduce a polar group, or polar heteroation which bridges the undecyloyl group and the addend group. A second polar group confers new and unusual properties on the adduct.

An example of a chain extending synthesis is the conversion of the vinyl moiety to a hydroxy amino chain. This is accomplished by first converting the vinyl group to the epoxide group with, for example, hydrogen peroxide, the causing the epoxide to react with a relatively long chain primary amine. Such a synthesis is illustrated by the following equations:

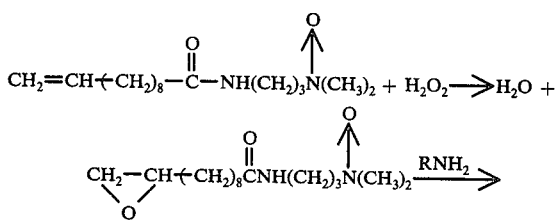

-continued

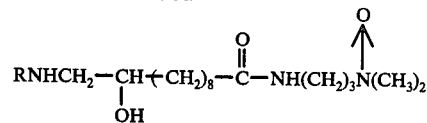

Other chain extending syntheses, but by no means all of the possibilities, are (a) The addition of alcohols to the double bond, (2) The addition of mercaptans to the double bond, and (3) The addition of hydrogen halide to the double bond, followed by reaction with a neucleophile such as an amine.

Furthermore, the presence of the terminal vinyl group permits the compound of this invention to be converted to an amphoteric sufactant by causing it to react with sodium sulfite, or by causing the hydrogen halide adduct to react with sodium sulfite. The following examples are illustrative of the present invention:

EXAMPLE 1

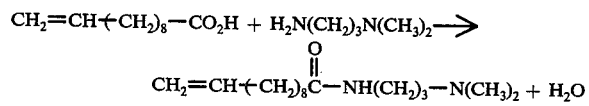

187.3 grams of undecylenic acid and 112 grams of 3-dimethylamino-n-propylamine were heated slowly until the temperature reached about 160°, and the mixture was kept at about that temperature for about 2 hours while unreacted amine and water slowly distilled out of the mixture. During this time, about 24 ml. of liquid distilled over. An additional 25 gm. of amine was added and heating and distillation continued for another 2 hours. Then the mixture was stripped of volatile material by heating in vacuo. At this point, titration showed that the material in the flask contained 1.9% of free undecylenic acid. The product was used in the next step, shown in Example 2, without further purification.

EXAMPLE 2

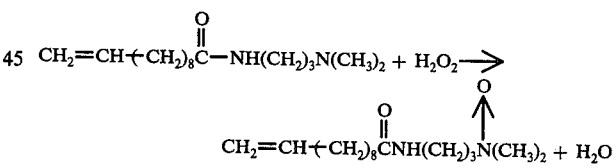

235 grams of the product from Example 1 were mixed with 88.8 grams of aqueous 35% hydrogen peroxide and 147 grams of water, and heated slowly to about 95° C. Since the mixture became very viscous, 50 grams of water was added; heating was continued for about 3 hours, while about 25 grams of water continued to be added every hour in order to reduce the viscosity. The final mixture, upon analysis, contained 37.45% active amine oxide, 0.46% of free amine and 0.03% of hydrogen peroxide.

The invention claimed is:
1. 10-undecylenoylamidopropyldimethylamine oxide.

* * * * *